United States Patent [19]

Adjei et al.

[11] Patent Number: 4,897,256
[45] Date of Patent: Jan. 30, 1990

[54] LHRH ANALOG FORMULATIONS

[75] Inventors: Akwete L. Adjei, Wadsworth; Edwin S. Johnson, Antioch; James W. Kesterson, Libertyville, all of Ill.

[73] Assignee: Abbott Laboratories, Abbott Park, Ill.

[21] Appl. No.: 114,359

[22] Filed: Nov. 4, 1987

Related U.S. Application Data

[63] Continuation-in-part of Ser. No. 934,874, Nov. 25, 1986.

[51] Int. Cl.$^4$ ............................................. A01N 25/02
[52] U.S. Cl. .......................................... 424/43; 424/45; 514/2
[58] Field of Search ........................... 424/43, 45; 514/2

[56] References Cited

U.S. PATENT DOCUMENTS

| | | | |
|---|---|---|---|
| 3,898,329 | 8/1975 | Said et al. | 514/12 |
| 4,110,434 | 8/1978 | Jolles et al. | 514/8 |
| 4,261,885 | 4/1981 | Sakakibara et al. | 530/311 |
| 4,405,598 | 9/1983 | Brown | 424/45 |
| 4,438,029 | 3/1984 | Erickson et al. | 530/327 |
| 4,462,983 | 7/1984 | Azria et al. | 424/45 |
| 4,476,116 | 10/1984 | Anik | 514/15 |
| 4,481,191 | 11/1964 | Web et al. | 514/14 |
| 4,504,470 | 3/1985 | Uda et al. | 514/19 |

FOREIGN PATENT DOCUMENTS

| | | |
|---|---|---|
| 1014471 | 7/1977 | Canada . |
| 0111841 | 6/1984 | European Pat. Off. . |
| 1454105 | 10/1976 | United Kingdom . |
| 2145107 | 3/1985 | United Kingdom . |

OTHER PUBLICATIONS

Luthi et al., "Enzymatic Synthesis of Hydrocarbon-Soluble Peptides with Reverse Micelle", J. Am. Chem. Soc. 106 7285–7286 (1984).

Markham et al., "Influence of Detergent on Aerosol Allergic Sensitization with Enzymes of Bacillus Subtilis", Int. Archs. Allergy Appln. Immun. 51 529–543 (1976).

Hirai et al., "Effect on Surfactants on the Nasal Absorption of Insulin in Rats", Int. J. Pharmaceutics 9 165–172 (1981).

Hirai et al., "Mechanisms for the Enhancement of the Nasal Absorption of Insulin by Surfactants", Int. J. Pharmaceutics 9 173–184 (1981).

Anik et al., "Delivery Systems for LHRH and Analogs", in LHRH And Its Analogs, eds. B. H. Vickery et al., 421–435 (1984).

Nillius et al., "Contraceptive Uses of GnRH Analogues", World Conf. Clin. Pharmacol. Ther. 2nd (1984).

Nillius et al., "LHRH Agonists for Female Contraception", in LHRH And Its Analogs, eds. B. H. Vickery et al., 207–217 (1984).

Sandow et al., "Intranasal Administration of Peptides Biological Activity and Therapeutic Efficacy", Transnasal Systemic Medications (ed. Y. W. Chien) 183–199 (1985).

Lambrie et al., "Contraception with LHRH Agonists, a New Physiological Approach", Repro-Reproduction 5 229–241 (1981).

Primary Examiner—Ellis P. Robinson
Assistant Examiner—P. J. Ryan
Attorney, Agent, or Firm—Steven R. Crowley; Steven F. Weinstock; Martin L. Katz

[57] ABSTRACT

The invention relates to novel solution and suspension aerosol formulations comprising LHRH analogs.

2 Claims, No Drawings

LHRH ANALOG FORMULATIONS

TECHNICAL FIELD

This is a continuation-in-part of pending U.S. patent application, Ser. No. 934,874, filed Nov. 25, 1986.

The invention relates to novel formulations comprising LHRH (luteinizing hormone releasing hormone) analogs and, more particularly, to LHRH analog aerosol formulations.

BACKGROUND ART

Polypeptides and LHRH analogs in particular are historically administered parenterally because they are poorly absorbed by biological membranes due to their large molecular size and polarity, enzymatic degradation and deactivation by proteases enroute to the circulatory system. To improve bioavailability, some have developed formulations for rectal and nasal administration. These two routes of administration yield bioavailability results of about 0–5% and are not reproducible. Thus, these routes are pharmaceutically unacceptable.

Further, to date no aerosol formulation has been developed for administration of LHRH analogs by inhalation. This is due in part because many peptide drugs such as LHRH agonist and antagonist compounds do not appreciably dissolve in hydrophobic liquid vehicles to enable preparation of solution aerosols. Further, since suspension aerosols require micronization of the LHRH analogs, usually in air for efficiency reasons, and the LHRH analogs are biologically hazardous in low concentrations, suspension aerosols of LHRH analogs have not been considered feasible.

For example, leuprolide is a polar nonapeptide with three ionizable sites, namely the imidazolyl nitrogen of histidine with pKa approximately 6.0, the phenolic hydroxyl of tyrosine with pKa approximately 10.0, and the guanidine nitrogen of arginine with pKa approximately 13.0. Since the guanidine nitrogen is extremely basic, this nonapeptide as synthesized exists in the protonated form and is generally associated with at least one mole of acetic acid. Leuprolide, therefore, exists as an acetate salt, which is highly hydrophilic.

LHRH analogs are practically insoluble in fluorocarbons. In mixtures of ethyl alcohol and fluorocarbons, the solubility of leuprolide approaches 3 mg/ml which is not satisfactory due to dose requirements. This solubility estimate is not significantly affected by the presence of nonionic surfactants because, in part, of solubility and dielectric limitations of such surfactants. In mixtures of fluorocarbons, ethyl alcohol and water, experimental results showed equilibrium solubility of leuprolide to approach 5 mg/ml which is still unacceptable. At high concentrations of ethyl alcohol, a gel-like mass forms resulting in a colloidal dispersion that does not clear at room temperature for up to one month. At water concentrations of 10% or greater, a complete phase separation occurs making a homogeneous formulation impractical and renders aerosolization impractical.

Preparing suspension aerosols requires micronization of the drug prior to manufacture of the aerosol. This process involves mechanical breakup of the powder using grinding or milling equipment to reduce drug particle size to below 10 microns which is essential for pulmonary deposition of the aerosol. Generally, this milling process results in significant exposure of the drug to the surrounding environment as well as up to 20% loss of the drug. The airborne LHRH analog particles can cause safety and health hazards if precautionary measures are not taken.

DISCLOSURE OF THE INVENTION

It has now been discovered that the foregoing and other problems with the prior art can be overcome by including lipophilic counterions in solvent-based, solution aerosol formulations. Further, the technical and safety hazards associated with preparing suspension aerosols can be overcome by liquid milling LHRH analogs and using a low boiling liquid propellant. Bioavailability of leuprolide, a prototype peptide in this invention, ranges from 50% to 100% of the intravenously administered product as a control formulation. Time for plasma peak concentration to occur is about 30 minutes, and the plasma peak concentration itself approximately equals that of a comparable dose administered intravenously.

In particular, the solution aerosol formulations for administration of LHRH analogs comprise:
1. LHRH analogs (active ingredient)
2. lipophilic counterion (solubilizing agent)
3. surfactant (wetting agent)
4. solvent
5. propellant and optionally
6. valve lubricant
7. antioxidant
8. flavor/fragrance.

More particularly, the preferred formulation of the invention is as follows:

| Ingredient | Ranges |
| --- | --- |
| Ethyl Alcohol, Dehydrated, U.S. Pat., 100 Proof | 0.50–60.00% w/w |
| Sorbitan Monooleate, NF | 0.05–6.00% w/w |
| Water, Purified, U.S. Pat. (Distilled) | 0.10–15.00% w/w |
| 1-Decane Sulfonic Acid Sodium Salt | 0.01–2.00% w/w |
| Leuprolide Acetate | 0.01–2.00% w/w |
| Dichlorodifluoromethane | q.s. |

The suspension aerosol formulations for administration of LHRH analogs comprise:
1. LHRH analogs (active ingredient)
2. surfactant (dispersing agent)
3. solvent (Freon 11 and/or Absolute alcohol)
4. propellant and optionally
5. surfactant (wetting agent and valve lubricant)
6. antioxidant
7. flavor/fragrance.

The preferred suspension formulation of the invention is as follows:

| Ingredient | Ranges |
| --- | --- |
| Trichlorofluoromethane | 0.00–55.00% w/w |
| Sorbitantrioleate | 0.05–10.00% w/w |
| Dichlorodifluoromethane | 30.00–99.00% w/w |
| Leuprolide Acetate | 0.01–5.00% w/w |

BEST MODE FOR CARRYING OUT THE INVENTION

The solution aerosol composition for administration of LHRH analogs by inhalation comprises:

| Ingredient | Range |
| --- | --- |
| LHRH Analog | .001–15 mg/g |
| Lipophilic Counterion | .05–10 mg/g |
| Surfactant | 0–5% w/w |
| Solvent (Water and Ethyl Alcohol) | 10–50% w/w |
| Propellant | q.s. |

The suspension aerosol composition for administration of LHRH analogs comprises:

| Ingredient | Range |
| --- | --- |
| Trichlorofluoromethane | 0.00–550 mg/gm |
| Sorbitantrioleate | 0.05–100 mg/gm |
| LHRH Analog | 0.01–50 mg/gm |
| Dichlorodifluoromethane | 30.00–990 mg/gm |

As used herein, "% w/w" refers to weight of ingredient per weight of formulation multiplied by 100.

As used herein, the term "LHRH analog" refers to octapeptides, nonapeptides and decapeptides including but not limited to leuprolide and D-amino acid analogs of LHRH. More particularly, LHRH analogs in addition to leuprolide (U.S. Pat. No. 4,005,063) which can be formulated in accordance with the invention include those which are described in U.S. Pat. Nos. 3,853,837, 3,972,859, 4,008,209, 4,024,248 (buserilin) 4,089,946 (lutrelin), 4,100,274 (goserelin), 4,234,571 (nafarelin), 4,490,291, and also includes histrelin.

As used herein, the term "leuprolide" or "leuprolide acetate" refers to a nonapeptide, 5-Oxo-L-prolyl-L-histidyl-L-tryptophanyl-L-seryl-L-tyrosyl-D-leucyl-L-leucyl-L-arginyl-L-prolylethylamide acetate with the structure:

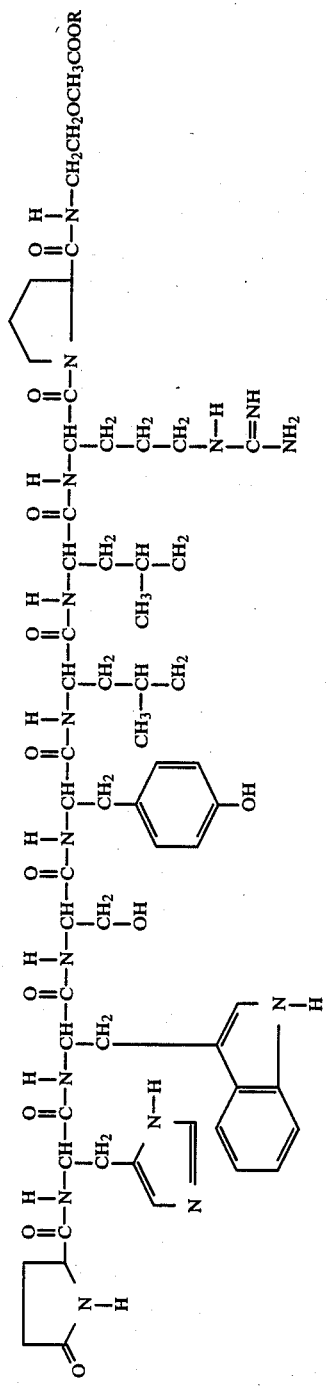

As used herein, the term "surfactant" refers to nonionic surfactants including but not limited to mono and diglycerides, sorbitan fatty acid esters, polyoxyethylene sorbitan fatty acid esters, polyoxyethylene sorbitol esters, polyoxyethylene acids, polyoxyethylene alcohols and polyoxyethylene adducts.

As used herein, the term "lipophilic counterion" or "counterion" refers to organic acids or their salts with pka sufficiently low to render them ionizable at the product pH and includes but is not limited to alkyl ($C_5$–$C_{12}$) sulfonic acids and salts thereof, palmitates, dioctylsulfosuccinate and its congeners, stearates and salicylates.

As used herein, the term "propellant" refers to chlorofluorocarbons or hydrocarbons including but not limited to trichlorofluoromethane, dichlorodifluoromethane, chlorodifluoromethane and dichlorotetrafluoroethane.

The presence of various lipophilic counterions significantly improves the equilibrium solubility of the LHRH analog in many cosolvent systems studied. Increasing concentrations of the counterion generally increases the solubility of LHRH analog in the propellant solvent systems. However, this is limited by the intrinsic solubility of the counterion itself. Thus, high concentrations of the counterion can be detrimental to the clarity and stability of the solution.

Optimal concentrations of the counterion of choice, decane sodium sulfonate, is 2 mg/ml. At this concentration, the equilibrium solubility of the LHRH analog in appropriate cosolvent mixtures of ethyl alcohol and dichlorodifluoromethane is about 20 mg/ml. However, a formulation containing 10 mg/ml of leuprolide appears to possess all desired physical characteristics of a satisfactory/stable aerosol.

In general, other lipophilic counterions also significantly improve the solubility of LHRH analogs in a propellant-water-ethanol cosolvent system. The most preferred counterions are: alkyl sulfonates followed by palmitates, dioctylsulfosuccinates, stearates and salicylates. These findings correlate with counterion pKa and appear to be consistent with drug distribution phenomena.

A solution aerosol containing approximately 25.0% w/w ethyl alcohol, 1.3% w/w sorbitan monooleate, 0.2% w/w decane sulfonic acid (sodium salt), 3.5% w/w water, 1.0% leuprolide acetate, and 69% w/w dichlorodifluoromethane is a preferred formulation for a leuprolide solution aerosol product. Most preferred is a solution aerosol containing approximately 20.0% w/w ethyl alcohol, 1.3% w/w/ sorbitan monooleate, 0.2% w/w decane sulfonic acid (sodium salt), 1.8% w/w water, 1.0% leuprolide acetate, and 75.7% w/w dichlorodifluoromethane. Both formulations have good spray characteristics and satisfactory physical and chemical stability.

The compositions of the invention can be prepared by cold filling or pressure filling.

Cold filling comprises the steps as follows:

(a) Mix alcohol and water in stainless steel or glass vessel.

(b) Add the counterion first and then the LHRH analog. Mix well until completely dissolved.

(c) Add surfactant. Mix well to dissolve.

(d) Filter through appropriate filter to clarify solution.

(e) Transfer to pressure vessel. Chill solution to approximately 0° C. or lower.

(f) Add appropriate propellant as liquefied gas. Mix well until a uniform solution forms.

(g) Fill into appropriate containers and check for leaks in warm water bath.

Pressure filling comprises the steps as follows:

(a) Mix alcohol and water in stainless steel or glass vessel.

(b) Add counterion first and then LHRH analog. Mix well until completely dissolved.

(c) Add surfactant. Mix well to form complete solution.

(d) Filter if necessary using appropriate filter.

(e) Fill appropriate volume into aerosol container and crimp valves onto container.

(f) Fill appropriate volume of liquified propellant into container through the valve. Check for leaks in warm water bath.

A preferred suspension aerosol contains approximately 10% w/w trichlorofluoromethane, 3% w/w sorbitan trioleate, 1.0% w/w leuprolide acetate, and 86% w/w dichlorodifluoromethane. This formulation has good spray characteristics and has satisfactory physical and chemical stability. This formulation can be prepared as follows:

(a) Add the leuprolide and glass or tungsten beads to the milling chamber (Dyno Mill obtained from Glen Mills, Inc., Maywood, N.J.).

(b) Add the trichlorofluoromethane and an appropriate amount of surfactant to the milling chamber.

(c) Close milling chamber tightly, and begin to chill the slurry to approximately −20° C.

(d) Mill the slurry by circulation either continuously or in batches until the particles are in the appropriate respirable size range.

(e) Empty the slurry into aerosol containers. Add propellant and crimp containers using either cold fill or pressure fill method.

(f) Check for leaks in warm water bath.

The foregoing may be better understood from the following examples which are presented for purposes of illustration and are not intended to limit the scope of the invention.

EXAMPLES 1–15

Following the cold filling procedure outlined above and utilizing the ingredients referred to at numbers 1–15 on Table 1, gave the solution aerosol compositions referred to in Table 1.

Solubility Testing

Weighed quantities of leuprolide and the counterion were placed into 20 ml glass vials provided with rubber stoppers and appropriate overseals. The measured quantities of the liquified propellants were added to the vials. In systems where water and/or alcohol were used, the appropriate volumes of these liquids were measured and added. The prepared vials were sealed and shaken to determine equilibrium concentration of the LHRH analog in these respective solvent systems.

Results of the limit solubility measurements obtained with leuprolide in the respective solvents are reported in Table 1. These solubility results are pharmaceutically acceptable. The results are reported as estimates since propellant pressures presented sampling problems which in turn prevented actual determination of the limit solubility for the LHRH analog and since these solutions were not saturated due to their high affinity for leuprolide acetate.

TABLE 1

Effect of Lipophilic Counterions on Leuprolide Solubility at 25° C.

| Example # | Water % v/v | Ethyl Alcohol, % v/v | Dichloro fluorocarbon % v/v | Counterion, % w/v DSASS | PA | DOSS | Solubility of leuprolide (mg/ml) |
|---|---|---|---|---|---|---|---|
| 1 | 4.0 | 50.0 | 46.0 | 0.2 | | | >10 |
| 2 | 4.0 | 50.0 | 46.0 | | 0.2 | | >5 |
| 3 | 4.0 | 50.0 | 46.0 | | | 0.2 | >8 |
| 4 | 4.0 | 45.0 | 51.0 | 0.2 | | | >10 |
| 5 | 4.0 | 45.0 | 51.0 | | 0.2 | | >5 |
| 6 | 4.0 | 45.0 | 51.0 | | | 0.2 | >8 |
| 7 | 4.0 | 40.0 | 56.0 | 0.2 | | | >10 |
| 8 | 4.0 | 40.0 | 56.0 | | 0.2 | | >5 |
| 9 | 4.0 | 40.0 | 56.0 | | | 0.2 | >6 |
| 10 | 4.0 | 35.0 | 61.0 | 0.2 | | | >10 |
| 11 | 4.0 | 35.0 | 61.0 | | 0.2 | | >5 |
| 12 | 4.0 | 35.0 | 61.0 | | | 0.2 | >6 |
| 13 | 4.0 | 30.0 | 66.0 | 0.2 | | | >8 |
| 14 | 4.0 | 30.0 | 66.0 | | 0.2 | | >5 |
| 15 | 4.0 | 30.0 | 66.0 | | | 0.2 | >6 |

DSASS = Decane Sulfonic Acid Sodium Salt
PA = Palmitic Acid
DOSS = Dioctyl Sulfosuccinate

Bioabsorption Testing

Healthy male beagle dogs (9-18 months old) were provided with free access to food during the entire study. There were three dogs of each sex in each treatment group. Body weight, food consumption and other pertinent clinical signs were monitored at a regular basis during the study. By surgical procedure, tracheal stoma was performed to each dog. On the day of the study, the dogs were administered solution aerosol of leuprolide acetate of Example 10 except with 0.5, 1.0. and 2.0 mg of leuprolide. Drug administration was carried out through 2 weeks. Leuprolide plasma concentrations was determined during day 1 of the study in order to evaluate bioabsorption of leuprolide from the aerosol. Blood samples of approximately 2-3 ml were obtained from the jugular vein and allowed to clot. After centrifugation, the serum fraction was removed and assayed for leuprolide using a radioimmunoassay technique. Relative absorption of leuprolide via the inhalation route of administration was estimated using mean historical data from representative intravenously administered formulations. Table II shows the results of the above testing and indicates virtually complete absorption of leuprolide.

TABLE II

Plasma Concentration of Leuprolide (Ng/ml) Following Inhalation Delivery of Leuprolide Aerosolized Formulation

| Dog No. | Plasma Concentrated (Ng/Ml) Over Time(Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 25.7 | 36.2 | 26.9 | 7.7 | 3.6 | 0.9 | 54.2 |
| 2 | 0.0 | 23.7 | 24.7 | 16.1 | 5.8 | 2.8 | 0.8 | 38.1 |
| 3 | 0.0 | 38.3 | 44.3 | 35.3 | 13.1 | 6.7 | 1.8 | 77.6 |
| 4 | 0.0 | 23.0 | 42.1 | 34.6 | 11.6 | 4.3 | 1.2 | 66.7 |
| 5 | 0.0 | 40.1 | 51.1 | 39.5 | 14.7 | 7.0 | 2.0 | 86.0 |
| 6 | 0.0 | 84.8 | 72.5 | 48.2 | 17.7 | 8.2 | 2.0 | 116.5 |
| Mean | 0.0 | 39.3 | 45.2 | 33.4 | 11.8 | 5.4 | 1.5 | 73.2 |
| S.D. | 0.0 | 23.5 | 16.1 | 11.0 | 4.4 | 2.2 | 0.6 | 27.2 |

Dose = 0.5 mg
Relative bioavailability = 87.4%

| Dog No. | Plasma Concentration (Ng/Ml) Over Time(Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 89.6 | 118.9 | 79.5 | 28.3 | 13.5 | 4.0 | 179.2 |
| 2 | 0.0 | 85.0 | 50.5 | 34.2 | 11.1 | 5.2 | 1.2 | 85.9 |
| 3 | 0.0 | 91.7 | 102.4 | 75.0 | 30.5 | 13.2 | 3.8 | 171.7 |
| 4 | 0.0 | 88.3 | 118.4 | 96.3 | 33.3 | 19.1 | 5.9 | 206.6 |
| 5 | 0.0 | 78.7 | 91.0 | 56.3 | 18.1 | 7.9 | 1.8 | 127.8 |
| Mean | 0.0 | 86.7 | 96.2 | 68.3 | 24.3 | 11.8 | 3.3 | 154.2 |
| S.D. | 0.0 | 5.1 | 28.1 | 23.8 | 9.3 | 5.4 | 1.9 | 47.5 |

Dose = 1.0 mg
Relative bioavailability = 92.1%

| Dog No. | Plasma Concentration (Ng/Ml) Over Time(Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 136.4 | 165.2 | 181.0 | 75.7 | 44.4 | 12.8 | 386.9 |
| 2 | 0.0 | 148.3 | 225.4 | 131.7 | 48.9 | 20.7 | 5.7 | 306.0 |
| 3 | 0.0 | 178.1 | 167.9 | 148.2 | 69.1 | 31.9 | 7.5 | 343.1 |
| 4 | 0.0 | 121.9 | 138.7 | 72.7 | 22.6 | 10.3 | 2.0 | 177.1 |
| 5 | 0.0 | 204.6 | 258.4 | 194.7 | 125.7 | 71.0 | 22.8 | 549.1 |
| 6 | 0.0 | 91.8 | 104.0 | 88.9 | 37.8 | 16.8 | 3.9 | 195.5 |
| 7 | 0.0 | 125.8 | 118.7 | 95.4 | 43.1 | 17.4 | 4.2 | 220.9 |
| Mean | 0.0 | 143.8 | 168.3 | 130.4 | 60.4 | 30.4 | 8.4 | 311.2 |
| S.D. | 0.0 | 37.5 | 56.1 | 47.1 | 34.0 | 21.2 | 7.2 | 131.0 |

Dose = 2.0 mg
Relative bioavailability = 93.1%

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. An aerosol formulation comprising 0.01-5% w/w/ LHRH analog, 0.05-10% w/w/ surfactant, 0-55% w/w/ solvent and 30-99% w/w/ propellant.

2. The formulation of claim 1 wherein the LHRH analog is leuprolide acetate, the surfactant is sorbitantrioleate, the solvent is trichlorofluoromethane and the propellant is dichlorodifluoromethane.

* * * * *